United States Patent [19]

Gianturco

[11] Patent Number: 4,687,468
[45] Date of Patent: Aug. 18, 1987

[54] IMPLANTABLE INSULIN ADMINISTRATION DEVICE

[75] Inventor: Cesare Gianturco, Champaign, Ill.

[73] Assignee: Cook, Incorporated, Bloomington, Ind.

[21] Appl. No.: 888,633

[22] Filed: Jul. 25, 1986

Related U.S. Application Data

[63] Continuation of Ser. No. 656,346, Oct. 1, 1984, abandoned.

[51] Int. Cl.$^4$ .............................................. A61M 5/00
[52] U.S. Cl. ...................................... 604/153; 604/9; 128/DIG. 12
[58] Field of Search ....................... 604/153, 8, 9, 131, 604/175, 891, 185, 246; 128/DIG. 12, DIG. 13

[56] References Cited

U.S. PATENT DOCUMENTS

| | | | |
|---|---|---|---|
| 3,527,220 | 9/1970 | Summers | 604/153 |
| 4,360,010 | 11/1982 | Finney | 128/79 |
| 4,360,019 | 11/1982 | Portner et al. | 604/891 X |
| 4,511,355 | 4/1985 | Franetski | 604/153 X |
| 4,525,165 | 6/1985 | Fischell | 604/891 |
| 4,544,371 | 10/1985 | Dormandy, Jr. et al. | 604/891 |

Primary Examiner—Stephen C. Pellegrino
Attorney, Agent, or Firm—Woodward, Weikart, Emhardt & Naughton

[57] ABSTRACT

A device for self-administration of a measured amount of insulin by a diabetic patient by means of digital pressure upon a subcutaneous pump implanted over the sternum.

6 Claims, 5 Drawing Figures

IMPLANTABLE INSULIN ADMINISTRATION DEVICE

This application is a continuation of application Ser. No. 656,346, filed Oct. 1, 1984, now abandoned.

BACKGROUND OF THE INVENTION

This invention relates to an implantable device for administering a measured amount of liquid, for example, insulin.

Various types devices are known for administering drugs to a patient. In certain situations it is necessary that drugs be administered parenterally on a repeated continuous basis as often as a number of times a day. For example, diabetes may require injections of insulin on the order of twice a day. Such injections are irritating to the skin and tend to cause infection particularly when they must be accomplished so often. There are in existence the following U.S. patents which may disclose prior art: U.S. Pat. Nos. 3,756,243 issued to Shulte; 3,827,439 issued to Shulte; 3,951,147 issued to Tucker; 4,013,074 issued to Siposs; 4,191,181 issued to Franetski; 4,261,341 issued to Hakim, 4,265,241 issued to Portner; 4,298,002 issued to Ronel; 4,360,019 issued to Portner and 4,373,527 issued to Fischell. Still another reference of interest is the publication *Medical Progress Through Technology* 680—Vol. 5 No. 4 (1978-05). The known devices suffer from a number of disadvantages. They are expansive and complicated in design. They require multiple daily injections. They are electric or electronic in nature. They involve moving parts.

SUMMARY OF THE INVENTION

One embodiment of the implantable device for administering a measured amount of liquid drug of the present invention might include a container of flexible material for storing the liquid drug. There is also provided means for percutaneously filling the container. The device further includes a pump having a resiliently compressible receptacle. A first check valve is connected between the container and the receptacle and allows flow only from the container toward the receptacle. A second check valve is connected to the receptacle and leads away from the receptacle for discharge in the body. The second check valve allows flow only from said receptacle for discharge in the body.

Objects of the invention are to provide a device which permits freedom from multiple daily injections of insulin.

Another object of the invention is to eliminate the use of electrical or electronic components within the body.

Still another object of the invention is to provide a low cost simple design which does not have moving parts and operates reliably.

Related objects of the invention are to provide a device which permits control of the amount of insulin administered by a properly instructed patient and to provide a device in which the insulin solution needs to be replenished at only long time periods, such as only once a week.

BRIEF DESCRIPTION OF THE DRAWINGS

The invention disclosed here will be understood better with reference to the following drawings in which.

DESCRIPTION OF THE PREFERRED EMBODIMENT

Figure 1:
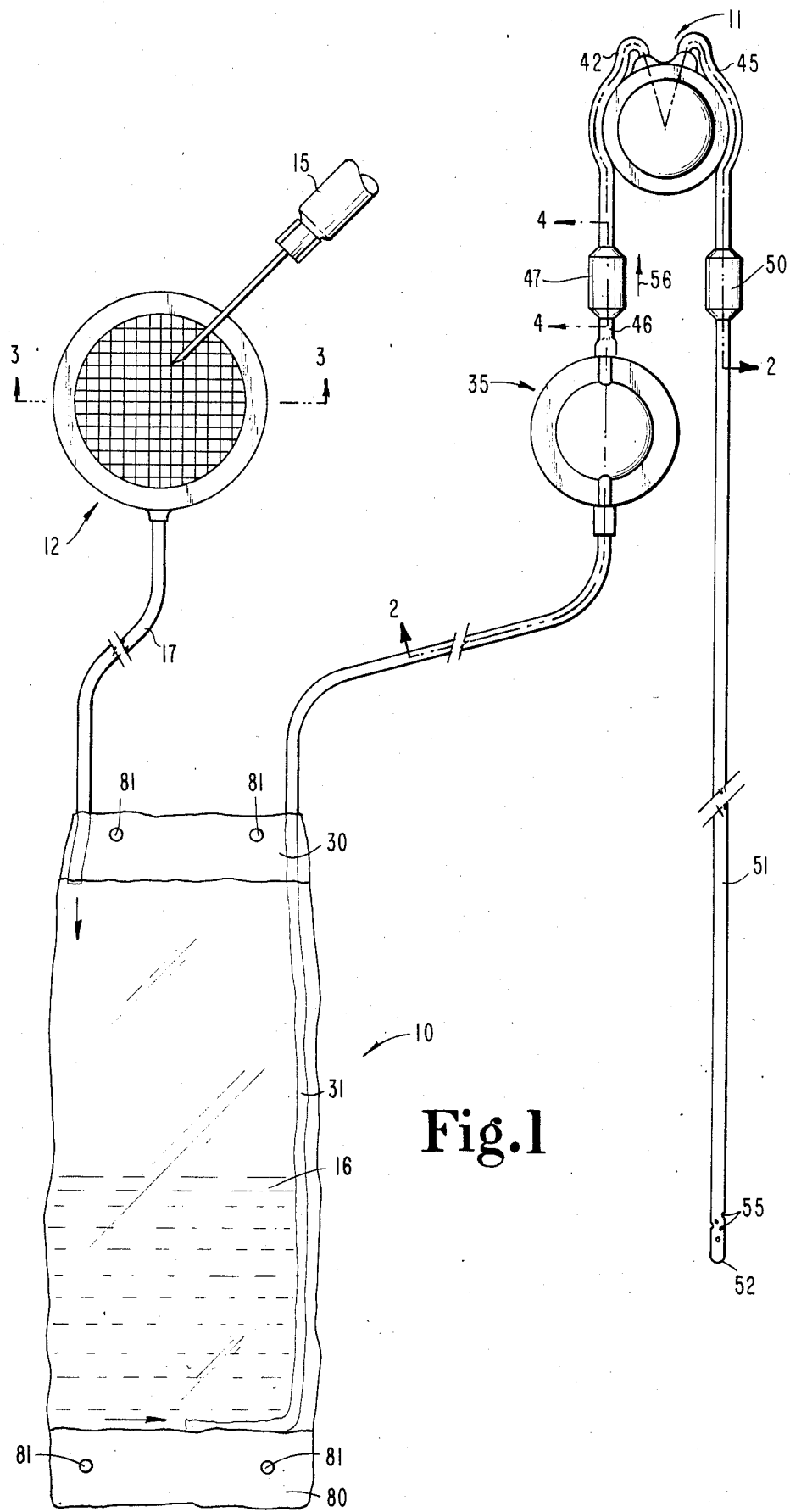
FIG. 1 is a front elevational view of the insulin administering device of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring more particularly to the drawing, there is illustrated an implantable device for administering a measured amount of insulin. The entire device 10 is implanted subcutaneously and permits the patient to administer a measured amount of insulin by depressing the pump 11. The pump 11 is positioned over the sternum 9 of the patient. The device further includes an access port or means 12 for percutaneously filling the container. As suggested by the showing of the hypodermic needle syringe 15, the access port 12 can be used on perhaps a once a week basis to inject a substantial portion of insulin into the sack or container 16.

Figure 3:
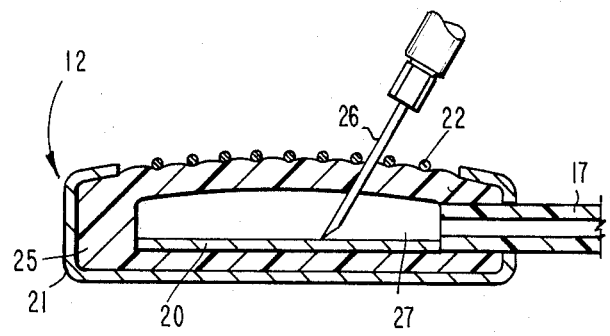
FIG. 3 is an enlarged section taken along the line 3—3 of FIG. 1 in the direction of the arrows.

The sack or container 16 is connected to the access port 12 by a flexible tubing section 17. With the exception of certain portions of the access port 12, all parts of the specific illustrated embodiment are constructed of inert plastic such as the compositions in physical character comparable to milled and compounded rubber prior to vulcanization but containing organo-silicon polymers, such as the composition sold under the trademark "Silastic". The access port 12, however, includes a needle stop disc and also a housing 21 as well as a grid 22. The access port 12 includes a Silastic housing 25 which is compressed within the stainless steel housing 21. The grid 22 is then mounted on the metal housing 21 so as to retain the Silastic 25 within the housing and to hold it in a compressed condition so that when the needle 26 is inserted through the grid the Silastic yields to permit passage of the needle yet when the needle is withdrawn the Silastic comes together and closes off the needle produced puncture. It can be seen from FIG. 3 the disk 20 functions as a stop to prevent the needle 26 from puncturing all the way through the container 25. The stop 20 also notifies the hypodermic needle operator that the tip of the needle is properly positioned. FIG. 3 also illustrates that the tubing 17 couples the hollow interior 27 of the access port 12 to the upper end 30 of the sack 16. The tubing 17 is attached to the Silastic housing 25 and the sack 16 by suitable adhesive.

When the insulin administrating device of the invention is implanted in the body, the access port 12 is located in the left lower quadrant of the abdomen. The sack 16 is implanted in the properitoneal fat so that it is subjected to peritoneal pressure. The tubing 17 from the access port opens in the upper part of the sack 16 while the outlet tubing 31 has its inlet end 32 in the center of the lower part of the sack 16. The tubing 31 is so arranged because the device is normally operated when the patient is in the erect or semi-erect position so that gravity will tend to pull the liquid toward the lower end of the sack 16. The flexible tubing 31 leads into an auxiliary pump 35. The auxiliary pump 35 has a pair of cup shaped members 36 and 37 joined together at their outer peripheries. Each of the cup shaped members has a concave side 40 and a convex side 41.

The construction of the pump 11 is generally the same as the construction of the pump 35. The pump 11 forms the primary pumping means for the device while the pump 35 forms an auxiliary pumping means. The pump 11 differs in construction from the pump 35 in that the flexible tubing sections 42 and 45 leading into and out of the pump 11 are secured to the sides of the pump 11 to generally retain the configuration and arrangement of the parts when the insulin administering device is implanted in the body.

Figure 2:
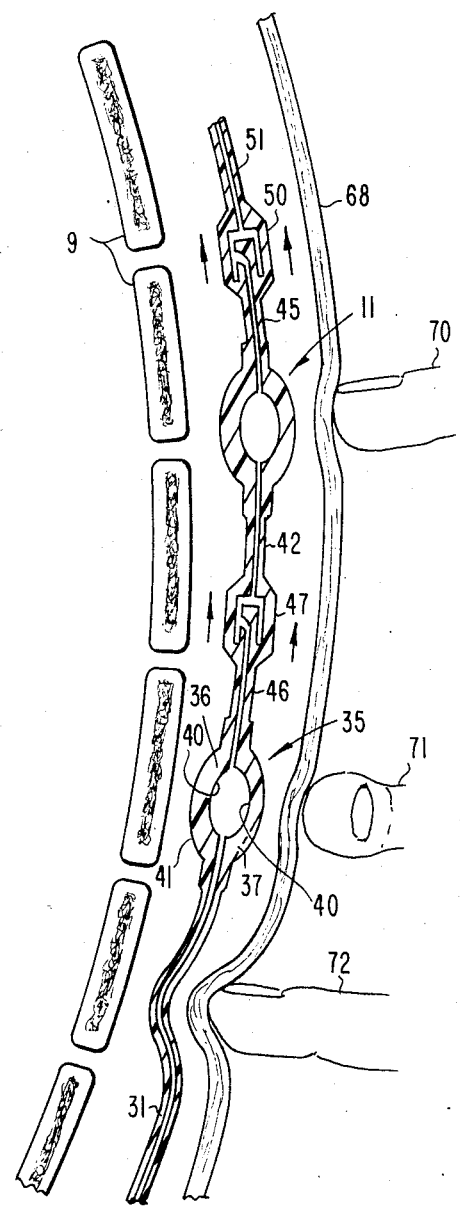
FIG. 2 is a section taken along the line 2—2 of FIG. 1 along the lumen of the device of FIG. 1. and showing how the device is implanted in the body of the patient and how the device is manipulated by the fingers of the patient.
Figure 4:
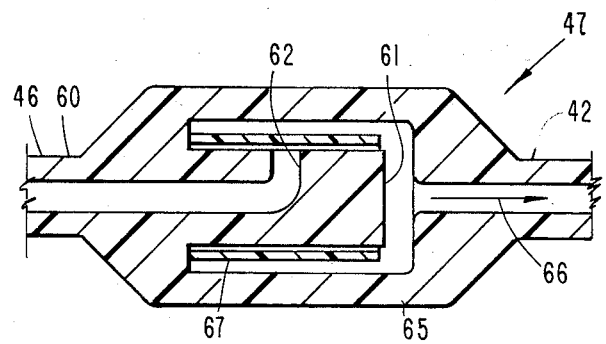
FIG. 4 is an enlarged section taken along the line 4—4 of FIG. 1 in the direction of the arrows.
Figure 5:
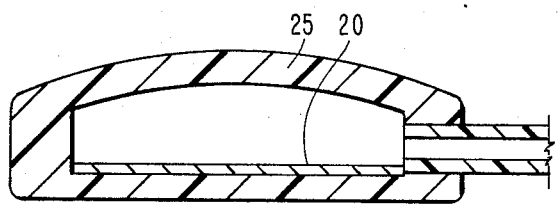
FIG. 5 is a view similar to FIG. 3 but showing the structure of FIG. 3 in an intermediate manufacturing step.

A further section 46 of tubing leads from the auxiliary pump 35 into the check valve 47. Still another check valve 50 is provided and is connected to the section of tubing 45 and also to a further section of tubing 51. The section of tubing 51 is closed at its end 52 and has a series of openings 55 in its wall at its distal end. The openings 55 are arranged to be positioned within the peritoneum so that the discharge location of the insulin is in the peritoneum. The check valves 47 and 50 are arranged so as to only permit flow of fluid in the direction of the arrows 56 and 57. The detail of construction of a representative one of the check valves 47 is shown in FIG. 4. The tube 46 has an external cylindrical surface 60 and a closed end 61. The tube 46 also has a passageway 62 which opens through the external cylindrical surface 60. A housing 65 surrounds the closed end and the passageway. The housing 65 is closed except for the discharge passageway 66 which connects to the section 42 of tubing. A short length 67 of flexible stretchable expandable tubular material is fixed to the tube 46 and covers the passageway 62. The length of material 67 is adapted to stretch and expand to permit flow of fluid to occur from the tube through the passageway 62 into the housing and out the discharge passageway 66. The flexible member on the other hand also is adapted to contract around the tube 46 and the passageway 62 to block flow from the housing into the passageway and tube when the pressure in the housing is greater than the pressure in the first passageway. As suggested in FIG. 2, the fingers of the patient are used to compress the pump 11 and the pump 35 by pressing against the skin 68. Pump 11 is the primary pumping means of the device. As long as the pump 11 is used at every meal, it will function reliably. It is possible that after being left idle for several days, the inlet valve 47 may stick and fail to function. For this reason the auxiliary pump 35 has been provided and may be used to force the inlet valve 47 open is the proximal tubing 31 is compressed to avoid a backward motion of the fluid. The patient's finger 72 is shown in position compressing the tubing 31 to prevent such backward motion. The finger 71 is shown in position to squeeze the pump 35 while the finger 72 compresses the tubing 31. As mentioned, the pump 35 is only a failsafe device and normally will not be needed to be used.

In normal operation at every meal the patient will compress the pump 11 by pressing the pump against the sternum 9 as suggested for the finger 70. This will cause the fluid within the pump to be expelled through the tubing section 45 and the check valve 50. Then when the pressure is released upon the pump causing the two cup shaped sides of the pump to move apart further fluid will flow into the pump through the check valve 47. The upper end 30 of teh sack and also the lower end 80 are made from cellular plastic material so as to give the upper and lower ends of the sack a relatively rigid construction. Also, two suture holes 81 are located at the upper end 30 and the lower end 80 of the sack for securing the sack in place.

Each of the sections of flexible tubing 31, 46, 42, 45 and 51 is secured to the components which it couples by appropriate adhesive. Thus the tubing 31 is connected to sack 16 and pump 35 by appropriate adhesive as is tubing 46 to check valve 47 and pump 35, as well as tubing 42 to pump 11 and check valve 47, as well as tubing 45 to pump 11 and check valve 50 and tubing 51 to check valve 50.

It will be evident from the above description that the insulin administering device of the present invention does provide freedom from multiple daily injections of insulin. It has been found that such a device need only be filled approximately once a week in order to provide sufficient insulin. The concentration of the insulin solution can be adjusted so that only a few pressures on the subcutaneous pump delivers the precise needed amount of protection at meal time.

It will also be evident from the above description that the present invention provides a reliable mechanical operation which does not involve electrical or electronic components. The present device is of simple construction and low cost and permits accurate control of the amount of insulin administered by a properly instructed patient. It should be mentioned that during one week a small amount of evaporation will occur in the system. It is therefore suggested that the water vapor probably in amount of 3-6 cc be aspirated along with any remaining old insulin before the weekly replenishment is accomplished.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An implantable device for administering a measured amount of liquid drug comprising:
   a container of flexible material for storing the liquid drug;
   a second container connected to said first mentioned container by tubing, said second container being made from inert plastic, a metal housing surround the inert plastic and maintaining it in a compressed condition, said housing having a metal grill permitting injection of a needle through the grill and the inert plastic into the second container for percutaneously filling the first mentioned container, a metal disc on the inside of said second conatiner as a stop for a needle;
   a pump including a pair of cup-shaped members, joined together at their peripheries, each of said cup-shaped members having a concave side and a convex side, the concave sides of said cup shaped members facing toward one another, the convex sides of said cup-shaped members facing away from each other; and, tubing means connecting said first mentioned container and said pump and leading away from said pump for discharge in the body.

2. An implantable device for administering a measured amount of liquid drug comprising:

a container of flexible material for storing the liquid drug;

a second container connected to said first mentioned container by tubing, said second container being made from inert plastic, a metal housing surround the inert plastic and maintaining it in a compressed condition, said housing having a metal grill permitting injection of a needle through the grill and the inert plastic into the second container for percutaneously filling the first mentioned container, a metal disc on the inside of said second conatiner as a stop for a needle; and a pump including a resiliently compressible receptacle, a first check valve connected between said first mentioned container and said receptacle and allowing flow only from said first mentioned container toward said receptacle and a second check valve connected to said receptacle and leading away from said receptacle for discharge in the body, said second check valve allowing flow only from said receptacle for discharge in the body.

3. The implantable device of claim 2 additionally comprising:

first flexible tubing connecting said second container and said first mentioned container;

an auxiliary pump including a second resiliently compressible receptacle;

second flexible tubing connecting said first mentioned container and said auxiliary pump;

third flexible tubing connecting said auxiliary pump and said first check valve;

fourth flexible tubing connecting first check valve and said first mentioned pump;

fifth flexible tubing connecting said first mentioned pump and said second check valve; and, sixth flexible tubing leading from said check valve for discharge in the body.

4. The implantable device of claim 2 additionally comprising flexible tubing connecting said second container to said first mentioned container, connecting said first mentioned container to said first check valve, connecting said first check valve to said pump, connecting connecting said pump to said second check valve, and leading from said second check valve for discharge in the body.

5. The implantable device of claim 3 wherein each of said check valves comprises a tube having an external cylindrical surface and a closed end, said tube having a first passageway which opens through the external cylindrical surface, a housing surrounding said closed end and said passageway, said valve housing being closed except for a discharge passageway, and a flexible, stretchable, expandable tubular member fixed to said tube and covering said passageway, said flexible tubular member being adopted to stretch and expand to permit flow to occur from said tube through said first passageway past said flexible tubular member into said valve housing and out said discharge passageway when the pressure in said first passageway is greater than the pressure in said valve housing, said flexible member being adapted to contract around said tube and said first passageway to block flow from said valve housing into said first passageway and tube when the pressure in said valve housing is greater than the pressure in said first passageway.

6. The implantable device of claim 3 wherein said first mentioned container has an upper end and a lower end, said second flexible tubing extending from the lower end of said first mentioned container to said auxiliary pump, cellular plastic reinforcing said upper and lower ends of said first mentioned container, said cellular plastic having suture holes therein for securing said first mentioned container within the properitoneal fat.

* * * * *